(12) United States Patent
Cerboni

(10) Patent No.: US 9,968,254 B2
(45) Date of Patent: May 15, 2018

(54) INTRAOCULAR PRESSURE MONITORING DEVICE

(75) Inventor: Sacha Cerboni, Lausanne (CH)

(73) Assignee: SENSIMED SA, Lausanne (CH)

( * ) Notice: Subject to any disclaimer, the term of this patent is extended or adjusted under 35 U.S.C. 154(b) by 455 days.

(21) Appl. No.: 13/520,242

(22) PCT Filed: Jan. 3, 2011

(86) PCT No.: PCT/EP2011/050038
§ 371 (c)(1),
(2), (4) Date: Sep. 26, 2012

(87) PCT Pub. No.: WO2011/083105
PCT Pub. Date: Jul. 14, 2011

(65) Prior Publication Data
US 2013/0041245 A1    Feb. 14, 2013

(30) Foreign Application Priority Data

Jan. 5, 2010 (EP) ................... PCT/EP2010/050062

(51) Int. Cl.
*A61B 3/16* (2006.01)
*A61B 5/00* (2006.01)
(52) U.S. Cl.
CPC .............. *A61B 3/16* (2013.01); *A61B 5/6821* (2013.01)
(58) Field of Classification Search
CPC ..................................................... A61B 5/00
(Continued)

(56) References Cited

U.S. PATENT DOCUMENTS 3,769,961 A * 11/1973 Fatt et al. ............... 600/356
3,958,560 A *  5/1976 March ..................... 600/319
(Continued)

FOREIGN PATENT DOCUMENTS

WO            03001991  A1    1/2003
WO       2009049686  A1    4/2009
WO    WO 2009049686  A1 *  4/2009

OTHER PUBLICATIONS

Matted Leonardi et al.; "Wireless contact lens sensor for intraocular pressure monitoring: assessment on enucleated pig eyes"; XP-002600763; Acta Opthaknikiguca 2009; LNKD-Pubmed:19016660, vol. 87, Nr. 4, pp. 433-437; ISSN: 1755-3768.

(Continued)

*Primary Examiner* — May Abouelela
(74) *Attorney, Agent, or Firm* — Bachman & LaPointe, P.C.

(57) ABSTRACT

An intraocular pressure monitoring device has a soft contact lens and a pressure sensor united with the contact lens, the pressure sensor comprising an active strain gage, a passive gage, a rigid element and a microprocessor. The active strain gage, passive gage and rigid element are placed at a distance from the center of the contact lens, the active strain gage comprising a portion encircling the center of the contact lens on at least 180°, wherein the passive gage and the rigid element each comprise a portion encircling the center of the contact lens on at least 180°, and wherein the portion of the passive gage situated around the center of the contact lens is placed in immediate vicinity of the portion of the rigid element situated around the center of the contact lens. A kit has such a pressure monitoring device and a portable recording device configured for communicating with the pressure monitoring device and for storing data received from it. An intraocular pressure monitoring system has such a kit and a computing device configured for communicating with the (Continued)

portable recording device for receiving and/or processing and/or storing data received from the portable recording device.

22 Claims, 4 Drawing Sheets

(58) Field of Classification Search
USPC ............ 600/398, 403, 404; 606/2; 604/540
See application file for complete search history.

(56) References Cited

U.S. PATENT DOCUMENTS

| | | | |
|---|---|---|---|
| 4,089,329 A * | 5/1978 | Couvillon et al. ............ | 600/398 |
| 4,922,913 A * | 5/1990 | Waters et al. ................ | 600/398 |
| 5,005,577 A * | 4/1991 | Frenkel ........................ | 600/398 |
| 6,193,656 B1 * | 2/2001 | Jeffries et al. ............... | 600/398 |
| 6,213,943 B1 * | 4/2001 | Abreu .......................... | 600/405 |
| 6,440,070 B2 * | 8/2002 | Israel ........................... | 600/398 |
| 6,443,893 B1 * | 9/2002 | Schnakenberg et al. ..... | 600/398 |
| 6,447,449 B1 * | 9/2002 | Fleischman et al. ......... | 600/405 |
| 6,579,235 B1 * | 6/2003 | Abita et al. .................. | 600/398 |
| 6,796,942 B1 * | 9/2004 | Kreiner et al. ............... | 600/398 |
| 7,137,952 B2 * | 11/2006 | Leonardi et al. ............. | 600/398 |
| 8,475,374 B2 * | 7/2013 | Irazoqui et al. .............. | 600/398 |
| 2002/0049374 A1 * | 4/2002 | Abreu .......................... | 600/405 |
| 2003/0078487 A1 * | 4/2003 | Jeffries et al. ............... | 600/398 |
| 2004/0186366 A1 * | 9/2004 | Leonardi et al. ............. | 600/398 |
| 2004/0207808 A1 * | 10/2004 | Fleischman et al. ..... | 351/160 R |
| 2007/0123767 A1 * | 5/2007 | Montegrande et al. ...... | 600/398 |
| 2008/0015421 A1 * | 1/2008 | Penner ......................... | 600/300 |
| 2009/0076367 A1 * | 3/2009 | Sit et al. ....................... | 600/398 |
| 2009/0203985 A1 * | 8/2009 | Ehrecke ....................... | 600/398 |
| 2010/0056935 A1 * | 3/2010 | McKinley et al. ........... | 600/504 |
| 2010/0234717 A1 * | 9/2010 | Wismer ........................ | 600/398 |
| 2010/0324476 A1 * | 12/2010 | Boukhny et al. .............. | 604/65 |
| 2011/0015512 A1 * | 1/2011 | Pan et al. ...................... | 600/399 |
| 2011/0184271 A1 * | 7/2011 | Veciana et al. ............... | 600/398 |

OTHER PUBLICATIONS

"MEMS, Microfluidics and Microsystems Executive Review"; XP-002600775; http://www.memsinvestorjournal.com/2009/02/applying-mems-technology-to-the-diagnosis-of-glaucoma-.html; MEMS Investor Journal, Weekly Newsletter; Feb. 19, 2009.

* cited by examiner

INTRAOCULAR PRESSURE MONITORING DEVICE

BACKGROUND

The present invention relates to a device for monitoring the intraocular pressure (IOP). The present invention relates in particular to a device that can be placed on the eye of a user to monitor intraocular pressure over an extended period of time, for example 24 hours or more. The present invention also relates to a kit and to a system for monitoring the intraocular pressure (IOP).

Glaucoma is a widespread disease characterized by an elevated intraocular pressure (IOP). This elevated IOP produces a gradual loss of peripheral vision. There is therefore a need to have a detailed knowledge of IOP in glaucoma patients in order to provide reliable diagnostics or for setting up new therapies.

Patent EP1401327 describes an intraocular pressure recording system comprising a soft contact lens and a pressure sensor fixed to the contact lens. The pressure sensor comprises an active strain gage which is located around the center of the contact lens, thus allowing measuring the spherical deformations of the eyeball that are due to IOP changes. In one embodiment, the pressure sensor comprises two active strain gages and two passive gages placed in a Wheatstone bridge configuration. The active strain gages are circular gages situated around the center of the contact lens, while the passive gages are placed essentially radially to the lens in order to minimize their deformation when the eyeball is deformed. The passive gages are made of several radial segments located on one side of the contact lens, which are interconnected by short and substantially tangential segments.

A drawback of this intraocular pressure recording system is that it is difficult to optimize the characteristics of the sensor without compromising the comfort of the user. For the passive gage to be as insensitive as possible to the deformations of the eyeballs, the radial segments should be as long as possible relative to the tangential segments. However their length is limited because if they reach too close to the center of the lens they lay within the sight of the user. And even if the length of the radial segments is correctly limited for a standard use of the contact lens, one can't exclude situations where the user's sight might be disturbed by the passive gages, for example if the contact lens accidentally only slightly slides on the eye, or in a dark environment, where the user's pupil is particularly dilated.

Another drawback of this intraocular pressure recording system is that the asymmetrical design of the passive gages relative to the center of the contact lens could lead to asymmetrical temporary or permanent deformations of the contact lens itself, which might then loose its spherical shape, thus resulting in discomfort for the user wearing the lens.

Still another drawback of the intraocular pressure recording system of EP1401327 is that the position and the shape of the passive gages are very different from those of the active strain gages. The influence of variations in environmental factors other than the IOP, for example of the temperature, the humidity, etc., on the physical properties of the passive gages might therefore differ significantly from the influence of the same variations on the physical properties of the active strain gages, thus inducing errors or inaccuracies when determining the IOP.

SUMMARY OF THE INVENTION

An aim of the present invention is therefore to provide an intraocular pressure monitoring device that can be worn over extended periods of time and in any situation without major discomfort for the user.

Another aim of the present invention is to provide an intraocular pressure monitoring device that delivers an accurate measurement of the IOP.

Still another aim of the present invention is to provide a kit and an intraocular pressure monitoring system that can deliver an accurate measurement of the IOP over an extend period of time.

These aims and other advantages are achieved by a device, a kit and a system comprising the features of the corresponding independent claims.

These aims are achieved in particular by an intraocular pressure monitoring device comprising a soft contact lens and a pressure sensor united with the contact lens, the pressure sensor comprising an active strain gage, a passive gage, a rigid element and a microprocessor. The active strain gage, passive gage and rigid element are placed at a distance from the center of the contact lens, the active strain gage comprising a portion encircling the center of the contact lens on at least 180°, wherein the passive gage and the rigid element each comprise a portion encircling the center of the contact lens on at least 180°, and wherein the portion of the passive gage situated around the center of the contact lens is placed in immediate vicinity of the portion of the rigid element situated around the center of the contact lens.

These aims are also achieved by a kit comprising such a pressure monitoring device and a portable recording device configured for communicating with the pressure monitoring device and for storing data received from it.

These aims are also achieved by an intraocular pressure monitoring system comprising such a kit and a computing device configured for communicating with the portable recording device for receiving and/or processing and/or storing data received from the portable recording device.

According to the invention, the intraocular pressure monitoring device comprising a rigid element for rigidifying a part of the contact lens, it allows placing the passive gage in vicinity of this rigid element around the center of the contact lens, thereby allowing the design of passive gages that do not impair the user's sight, and also allowing the design of passive gages with a configuration similar to that of the active gage in order to provide for a more efficient and reliable correction of the variations measured by the active gage that are due to environmental factors and not to IOP variations.

The passive gage being placed in immediate vicinity of the rigid element, its shape can be freely chosen without almost any constraint, because its resistance to deformations of the eyeball of a user wearing the device of the invention is provided by the rigid element rather than by its shape and/or position or orientation on the contact lens. This allows for example designing a passive gage situated around the center of the contact lens, which is essentially symmetrical relative to the center of the contact lens. Furthermore, the passive gage can be designed and positioned similarly to the active strain gage. The passive gage can for example be an essentially continuous conductor, for example circular or polygonal, which is at least partly situated around the center of the lens. The passive gage can then easily be placed at a distance from the center of the contact lens sufficient for not disturbing the user.

BRIEF DESCRIPTION OF THE DRAWINGS

The present invention will be better understood with the help of the following description illustrated by the figures, where.

The same reference numbers in different figures designate the same or similar elements.

DETAILED DESCRIPTION OF THE PREFERRED EMBODIMENT(S)

Figure 1:
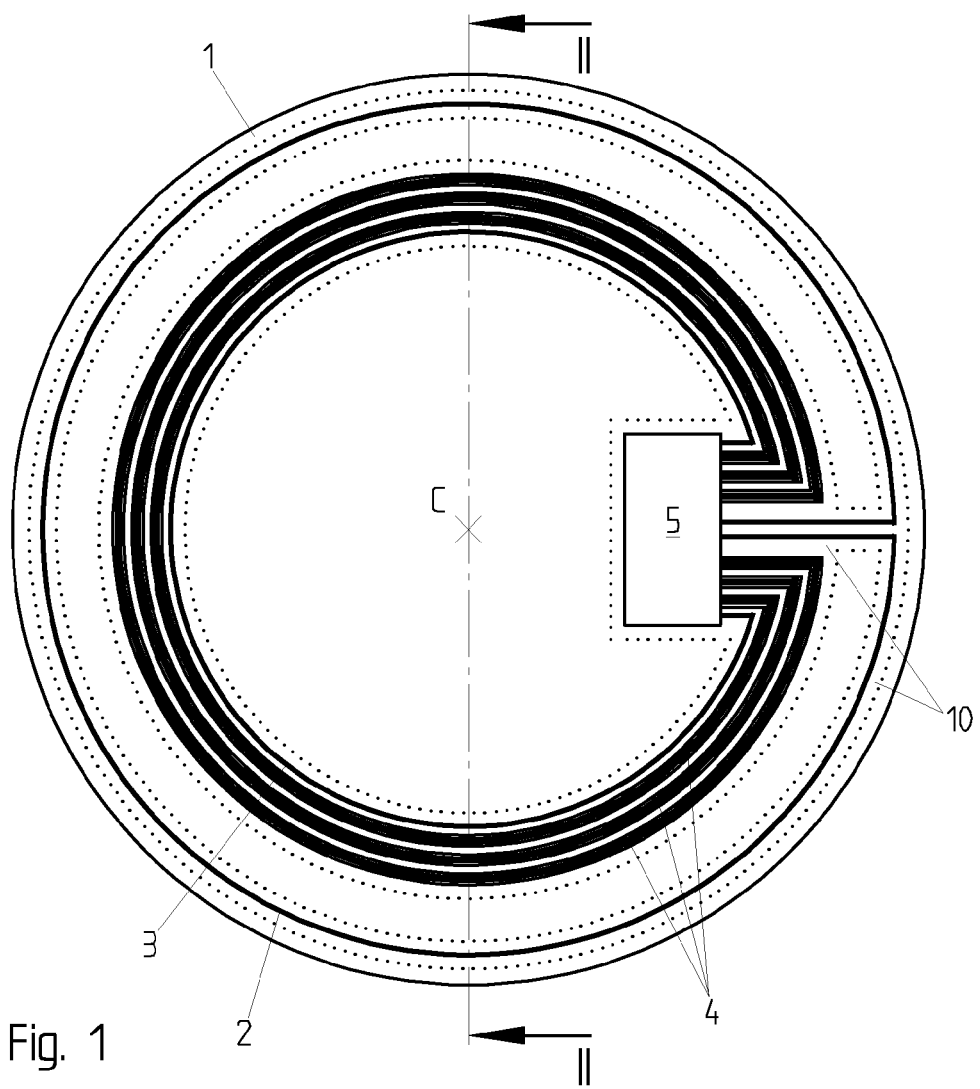
FIG. 1 illustrates an intraocular pressure monitoring device according to a preferred embodiment of the invention.

According to a preferred embodiment illustrated in FIG. 1, the intraocular monitoring device of the invention comprises a pressure sensor united with a contact lens 1, preferably a soft contact lens. When the contact lens 1 is worn by a user, the pressure sensor is placed on the eyeball of the user. In order to avoid any discomfort for the user, the elements of the pressure sensor are preferably not in direct contact with the eye. The sensor is for example incorporated, or embedded, within the contact lens 1 or affixed to the external, convex, surface of the contact lens 1, or a combination thereof, some elements of the sensor being embedded within the contact lens 1 and others being affixed on its surface.

However, according to other, less advantageous, embodiments of the invention, part or all elements of the pressure sensor are affixed on the inner, concave, surface of the contact lens 1 and are thus at least partly in direct contact with the eye of the user wearing the contact lens 1.

The elements of the pressure sensor are preferably all placed at a distance from the center C of the contact lens 1 sufficient for them to not disturb the eyesight of a user wearing the device of the invention, so that the device of the invention can be worn without significant disturbances and/or discomfort for the user over extended period of times, for example 10 hours, 24 hours or even some days, just like any usual contact lens.

The pressure sensor comprises an active strain gage 2, a passive gage 3, a rigid element 4 and a microprocessor 5.

The contact lens 1 is preferably a soft contact lens, made for example of a waterproof and/or silicone-based material, which adheres to the eyeball with a relatively high adhesion force. Variations of the intraocular pressure (IOP) generate deformations of the eyeball of a user. Typically, when the IOP rises, the eyeball dilates, and when the IOP diminishes, the eyeball contracts. When the device of the invention is worn by the user, the deformations of his or her eyeball induce deformations of the contact lens 1 that is in close contact with the eyeball, the amplitude of the deformations of the contact lens 1 being larger at its periphery.

The active strain gage 2 is configured and located on the contact lens 1 in order to be subjected to the deformations of the contact lens 1. According to the invention, a portion of the active strain gage 2 is placed around the center C of the contact lens 1 and at least partly encircles the center C. The active strain gage 2 thus describes, or covers, an arc of circle that is preferably centered on the center C of the contact lens 1.

The general shape of the portion of the active strain gage 2 that is placed around the center C is that of an arc of a circle. However, the configuration of this portion can vary within the frame of the invention, depending for example on the sought electrical properties of the active strain gage 2, the method used for its manufacturing, the place available on the contact lens, etc. The portion of the active strain gage 2 that is placed around the center C is for example made of one or more curved or circular segments forming one or more concentric arcs, or of one or more rectilinear segments forming for example one or more parts of a polygon, a mesh or any other adapted shape. A combination of one or more of the above shapes is also possible within the frame of the invention.

Independently of its configuration, the portion of the active strain gage 2 that is placed around the center C preferably covers an arc of at least 180° degrees around said center C, thus encircling the center C on at least 180°, i.e. on at least the half of its periphery, in order to provide for a sufficient and reliable sensing of the contact lens's deformations that are due to IOP variations, and thus in order to provide for a reliable measurement of IOP variations.

IOP variations induce deformations of the contact lens 1 worn by the user. The contact lens 1 is stretched when the IOP rises and contracted when it is reduced, or diminishes, thereby implying a variation of the contact lens's diameter. In order to reliably detect these diameter variations, the portion of the active gage 2 that is placed around the center C thus preferably covers an arc of at least 180°. This allows the active gage 2, independently of its local configuration, to detect diameter variations of the contact lens 1 rather than local deformations that could be due to local conditions that are not related to IOP variations.

Even more preferably, in order to maximize the length of the portion of the active strain gage 2 that is placed around the center C, thereby maximizing the sensitivity of the active strain gage 2, the portion of the active strain gage 2 that is placed around the center C covers as much as possible of an entire circle around the center C. According to a preferred embodiment of the invention, the portion of the active strain gage 2 that is placed around the center C thus preferably encircles the center C of the contact lens 1 on at least 270°, i.e. covering an arc of at least 270° degrees around said center C, a segment of the contact lens 1 being used by the essentially radial connections of the active strain gage 2 and of other elements of the pressure sensor to the microprocessor 5.

In a preferred embodiment, the active strain gage is a relatively thin and essentially circular electrical conductor placed at the periphery of the contact lens 1. Both ends of the active strain gage 2 are in electrical contact with the microprocessor 5. The section of the portion of the active strain gage 2 that is placed around the center C of the contact lens 1 is chosen small enough for the active stain gage to be deformable when submitted to the effects of the IOP variations. Preferably, the elasticity of the active strain gage 2 is equal or close to the elasticity of the contact lens 1. Even more preferably, the elasticity of the active strain gage 2 is equal to or higher than the elasticity of the contact lens 1. The active strain gage 2 is preferably made by etching, embossing and/or cutting of a thin metallic foil. In a variant embodiment, the active strain gage 2 is made of a thin metallic wire. In still a variant embodiment, the active strain gage is made by deposition of metal and/or of any other electrically conducting material, onto a preferably flexible and transparent substrate, for example onto a polyimide film 10.

According to the invention, and as explained above, the active strain gage 2 being united to the contact lens 1, deformations of the contact lens 1 induce deformations of the active strain gage 2, thereby modifying its physical properties, in particular its electrical properties. For example, if the IOP rises and the eyeball dilates, the contact lens 1 is extended at its periphery and the active strain gage 2 is stretched. This creates a diminution of the section of the portion of the active strain gage 2 placed around the center C of the contact lens 1 and thus an augmentation of its electrical resistance. By measuring the variations of the electrical resistance of the active strain gage 2 it is thus possible to detect and measure variations of the IOP.

The microprocessor 5 is programmed to measure the electrical resistance of the active strain gage 2 using methods known in the art.

Other factors than the deformation of the eyeball, and thereby of the contact lens 1, might however affect the electrical resistance of the active strain gage 2, in particular environmental parameters such as the temperature, the humidity, the ambient pressure, etc.

According to the invention, the pressure sensor of the invention comprises a passive gage 3 for measuring the effects of these other factors only, in particular for measuring the effects of the environmental parameters. According to the invention, the passive gage 3 is preferably similar in nature and configuration to the active strain gage 2, such that the effects of the environmental parameters on its physical properties are the same as or at least similar to the effects of these same parameters on the physical properties of the active strain gage 2. In particular, the passive gage 3 is preferably made of the same material and according to the same technology, or manufacturing process, as the active gage 2, and the shape and configuration of the passive gage 3 are preferably the same as or at least similar to the shape and configuration of the active gage 2. The passive gage 3 thus also comprises a portion placed around the center C of the contact lens 1 that preferably covers an arc of an angle close to the angle of the arc covered by the active gage 2.

According to the example illustrated in FIG. 1, the passive gage 3 is for example a thin and essentially circular electrical conductor placed around the center C of the contact lens 1. The passive gage 3 is preferably located closer to the center C of the contact lens 1 than the active strain gage 2. Both ends of the passive gage 3 are in electrical contact with the microprocessor 5.

Other configurations of the passive gage 3 are possible within the frame of the invention, the configuration of the passive gage 3 being preferably, but not necessarily, similar to that or the active gage 2. In particular, the portion of the passive gage 3 that is placed around the center C is for example made of one or more curved, or circular, segments forming one or more concentric arcs, or of one or more rectilinear segments forming for example one or more parts of a polygon, a mesh or any other adapted shape. A combination of one or more of the above shapes is also possible within the frame of the invention.

According to preferred embodiments of the invention, the passive gage 3 is of a configuration similar to that of the active gage 2, and preferably covers an arc with an angle close to the angle of the arc covered by the active strain gage 2, i.e. the passive gage 3 preferably encircles the center C of the contact lens 1 on an angle close to the angle with which the active gage 2 encircles the center C of the contact lens 1. The deformations induced in the passive gage 3 by possible variations of the environmental conditions are thereby similar to those induced by these same variations in the active gage 2. The effects of the variations of the environmental conditions on the electrical properties of the passive gage 3 are thus representative of the effects of the variations of the same environmental conditions on the electrical properties of the active gage 2.

The portion of the passive gage 3 that is placed around the center C of the contact lens 1 thus preferably covers an arc of at least 180°, i.e. encircles the center C of the contact lens on 180°. Even more preferably, the portion of the passive gage 3 that is placed around the center C covers an arc of at least 270° degrees around said center C, i.e. encircles the center C of the contact lens on at least 270°.

In order to avoid, or at least to minimize, any deformation of the passive gage 3 due to IOP variations, the pressure sensor of the invention further comprises a rigid element 4 having a portion located around the center C of the contact lens 1. The rigid element 4 is preferably sufficiently rigid for not being subjected to significant deformations when the user's eyeball is deformed. According to the invention, the portion of the passive gage 3 placed around the center C of the contact lens 1 is in immediate vicinity of the portion of the rigid element 4 placed around the center C of the contact lens 1. The portion of the passive gage 3 placed around the center C of the contact lens 1 is thus located in a region of the contact lens 1 that is rigidified by the rigid element 4 and is as such not, or only marginally, subjected to deformations due to IOP variations. The physical properties of the passive gage 3 are thus not noticeably modified when the eyeball is deformed because of IOP variations. Any noticeable change of the physical properties of the passive gage 3, in particular of its electrical resistance, can thus be considered as being due to other factors, in particular to variations of the environmental parameters.

The variations of the physical properties measured on the active strain gage 2 can thus be corrected by the variations of the physical properties measured on the passive gage 3 in order to determine the variations that are indeed essentially due to IOP variations. The variations of the intraocular pressure are thus determined for example on the basis of the result of the subtraction, from the measured variations of the electrical resistance of active strain gage 2, of the measured variations of the electrical resistance of passive gage 3, possibly multiplied or otherwise corrected by a calibration factor.

In the present description, the term "active strain gage", or "active gage", designates a strain gage of the pressure sensor of the device of the invention that is used for sensing deformations of the user's eyeball, and thus of the contact lens, that are due to variations of the user's IOP. The active strain gage is thus configured and placed on the device of the invention, in particular on the contact lens, in order to be as sensitive as possible to these deformations.

The term "passive strain gage", or "passive gage", however designates a strain gage of the pressure sensor of the device of the invention that is as insensitive as possible to the deformations of the eyeball that are due to variations of the user's IOP. Possible variations of the passive strain gage's physical properties are thus preferably due to variations of the environmental conditions only. The term "passive" thus refers to the fact that the strain gage only measures variations that are due to environmental conditions and is only marginally subjected to deformations due to the IOP variations.

According to the preferred embodiment illustrated in FIG. 1, the rigid element 4 is an antenna made for example of three concentric conductors placed around the center C of the contact lens 1, each made of a circular segment and each in electrical contact on both ends with the microprocessor 5. The antenna for example allows wirelessly transmitting signals between the microprocessor 5 and an external controller for measuring and recording the IOP variations over time. Preferably, the antenna 4 further allows providing electrical power to the microprocessor 5 through known induction powering methods.

According to an embodiment of the invention, when the microprocessor 5 is powered, the electrical resistance of both the active strain gage 2 and the passive gage 3 is measured, and possibly processed in the microprocessor 5 in order to determine an IOP value, either an absolute or a relative IOP value. The measured resistance values and/or the determined IOP value are then sent over the antenna 4 to the external controller for processing and/or for logging. Preferably, measurement cycles are initiated by the external controller and performed at regular intervals in order to allow a regular monitoring of the intraocular pressure. The frequency of the IOP measures depends on the needs, for example for diagnostic and/or experimental purposes, and is preferably determined by configuring the external controller.

In the preferred embodiment illustrated in FIG. 1, the rigid element 4 is an electrically conductive element paced around the center C and concentric with the passive gage 3 and the active strain gage 2. The configuration of the portion of the rigid element 4 that is located around the center C is preferably similar to that of the gages 2, 3, but with a significantly larger section, which makes it less elastic than the gages 2, 3 and thus preferably resistant to the deformations of the eyeball due to IOP variations. The rigid element 4 furthermore for example serves as an antenna for the pressure sensor to wirelessly communicate with an external controller.

The active strain gage 2 preferably lies along the periphery of the contact lens 1, where the amplitude of the deformations of the contact lens 1 due to IOP variations is the largest. The rigid element 4 and the passive gage 3 are preferably closer to the center C than the active strain gage 2, whilst not interfering with the eyesight of a user wearing the device of the invention. The rigid element 4 thereby rigidifies a central portion of the contact lens 1. Preferably, the passive gage 3 is situated in immediate vicinity of the rigid element 4, preferably along the inner side of the rigid element 4. In a variant embodiment, the passive gage 3 is at least partly situated between two concentric parts of the rigid element 4, for example between two rings of the antenna.

Other types of rigid elements are however possible within the frame of the invention in order to rigidify the part of the contact lens where the passive gage is located. In particular, the rigid element can have no other function than a mechanical one. The rigid element can for example be an element with a very low elasticity, placed in the immediate vicinity of the passive gage 3, or even attached to it, the rigid element being for example a relatively rigid substrate on which the passive gage 3 is affixed or grown through deposition, for example through metal vapour deposition. The rigid element is for example a rigid plastic, synthetic, metallic, or any other element with no other function than that of rigidifying a part of the contact lens in order to preserve the passive gage from deformations due to IOP variations when the device of the invention is worn by a user. According to a variant embodiment, the rigid element is for example a part, preferably in the form of a disc or a ring, of the contact lens 1, which is made more rigid than the rest of the contact lens, for example through a locally greater thickness and/or through the local use of another more rigid material than the material used for the rest of the preferably soft contact lens.

Figure 2:
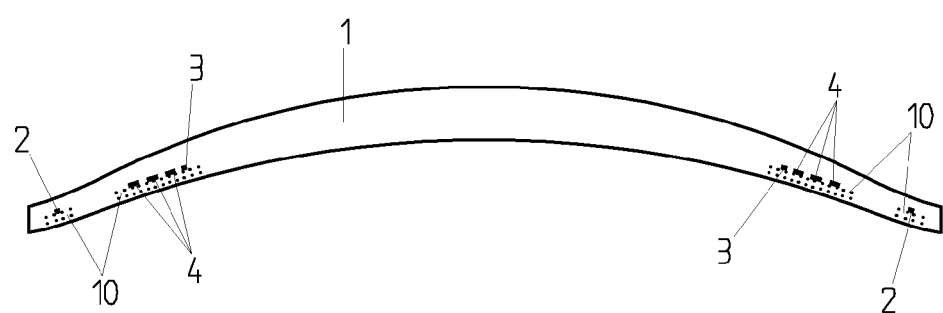
FIG. 2 is a cut view of the device of FIG. 1 along the II-II line.

In the preferred embodiment illustrated in FIGS. 1 and 2, the elements of the pressure sensor are assembled on a substrate 10, for example a polyimide film, and the pressure sensor is incorporated, or embedded, into the material forming the contact lens 1. In a variant embodiment, the pressure sensor, with or without substrate, is glued or otherwise affixed onto a side of the contact lens 1, preferably onto its external, convex, side.

Figure 3:
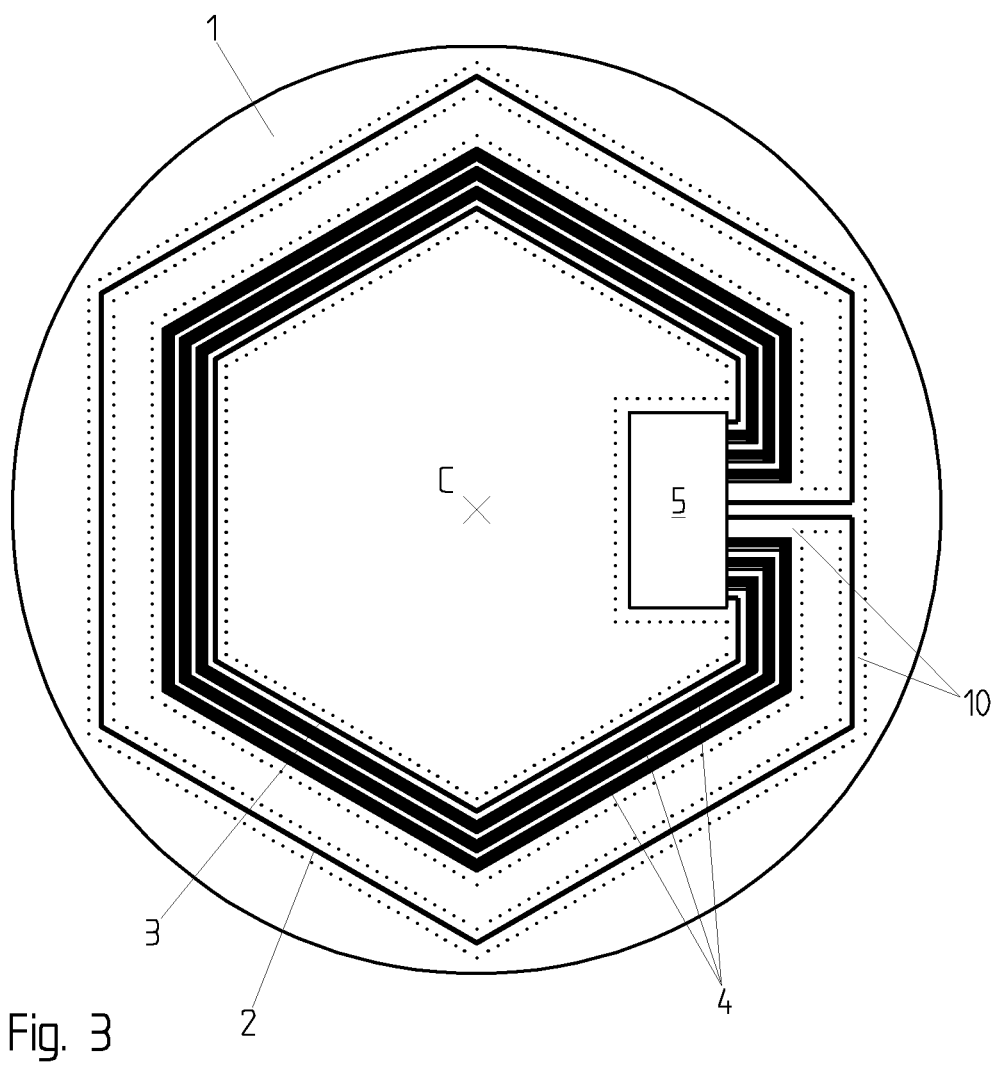
FIG. 3 illustrates an intraocular pressure monitoring device according to another embodiment of the invention.

In the preferred embodiment illustrated in FIG. 1, the portions of the active strain gage 2, of the passive gage 3 and of the rigid element 4 that are located around the center C of the contact lens are essentially made of one or more circular segments. Other shapes are however possible within the frame of the invention. In particular, these elements can be essentially polygonal, for example a portion of a hexagon, an octagon or a dodecagon. FIG. 3 for example shows a variant embodiment of the device of the invention, wherein the portions of the active strain gage 2, of the passive gage 3 and of the rigid element 4 that are located around the center C of the contact lens are made of a plurality of rectilinear segments forming polygons. In this example, each of these portions is configured as one or more concentric polygons, in particular as one or more almost complete regular hexagons. The hexagons are only partly complete because a segment of the contact lens 1 accommodates the radial connections of the gages 2, 3 and of the rigid element 4 to the microprocessor 5.

Figure 4:
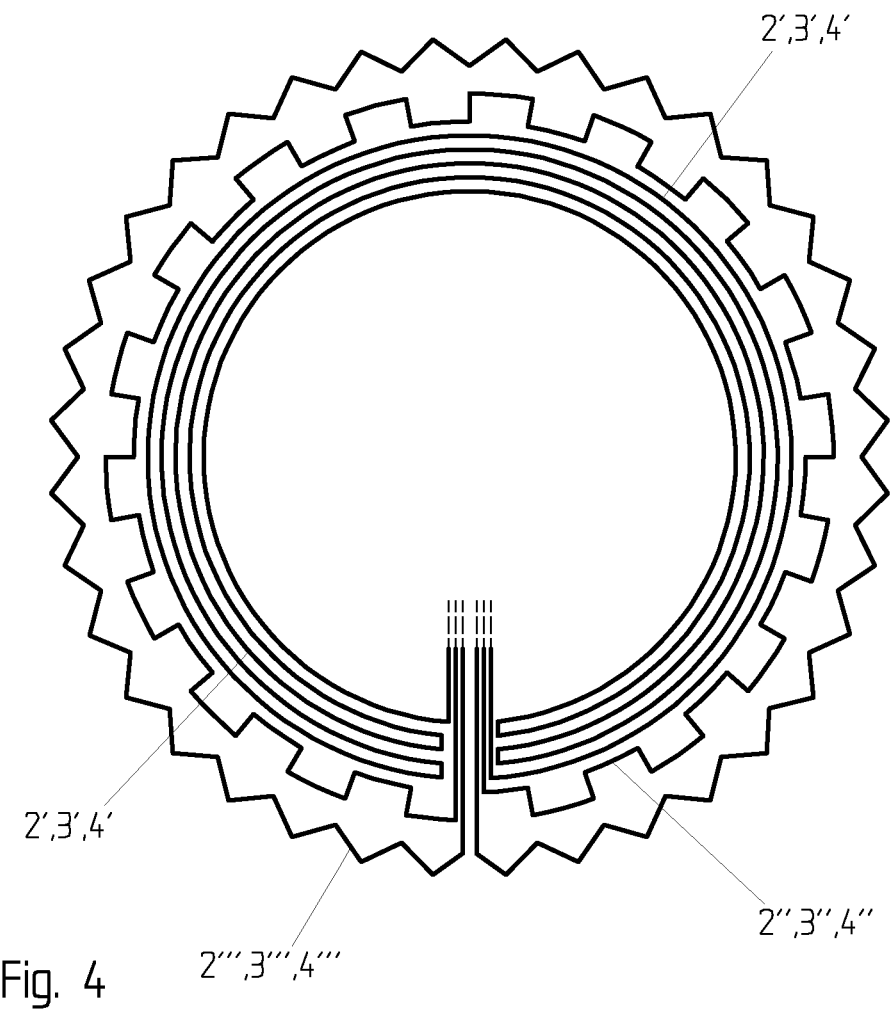
FIG. 4 shows an example of a possible configuration of a passive and/or of an active strain gage according to the invention.

FIG. 4 shows further illustrative but not limiting examples of possible configurations, or shapes, for the portions of the active strain gage 2, of the passive gage 3 and/or of the rigid element 4, that are located around the center C.

Preferably, the active strain gage 2, the passive gage 3 are made of any sufficiently conductive material, such that variations of its resistance due to small deformations can still be reliably measured with usual techniques. Such material can be any conductive metal, alloy comprising one or more of these metals, polysilicon or semiconductor material. In a preferred embodiment, the active strain gage 2 and the passive gage 3 are made of platinum. The rigid element 4 is possibly made of the same material as the gages 2, 3, in particular if it also has an electrical function over the mechanical one. The substrate 10 is preferably made of a non-conductive material, for example polyimide, parylene or benzocyclobutene (BCB).

Preferably, the active strain gage 2 and the passive gage 3 have sections of 10 to 100 micrometers width and 100 to 500 nanometers thickness, more preferably of 10 to 20 micrometers width and 100 to 200 nanometers thickness. According to the embodiment illustrated in FIGS. 1 and 2, each conductor of the rigid element 4 preferably has a section of 50 to 500 micrometers width and 1 to 50 micrometers thickness, more preferably of 150 to 250 micrometers width and 5 to 15 micrometers thickness. The thickness of the substrate 10, if any, is preferably between 1 and 500 micrometers, even more preferably between 5 and 10 micrometers. The use of other shapes, sections and/or thicknesses is however possible within the frame of this invention.

For the sake of readability and simplicity, the pressure monitoring device of the invention illustrated in FIG. 1 comprises one active strain gage 2 and one passive strain gage 3. It is however possible within the frame of the invention to provide a pressure sensor according to the invention with two or more active and/or passive strain gages. In particular, according to an advantageous configuration, the pressure sensor of the pressure monitoring device of the invention comprises two passive gages and two active strain gages that are interconnected in a Wheatstone bridge configuration, thereby allowing for a more efficient and reliable measurement of the IOP variations.

For the sake of readability and simplicity of the figures, the active strain gage 2 and the passive strain gage 3 are illustrated in their simplest form, i.e. their portion situated around the center C of the contact lens 1 is made of a single conductor that is electrically connected on both ends with the microprocessor 5. It is however possible, within the frame of the invention, to configure the portion of the passive and/or active gages situated around the center C with two or more concentric loops, each encircling the center C on an angle of at least 180°, preferably at least 270°.

Figure 5A:
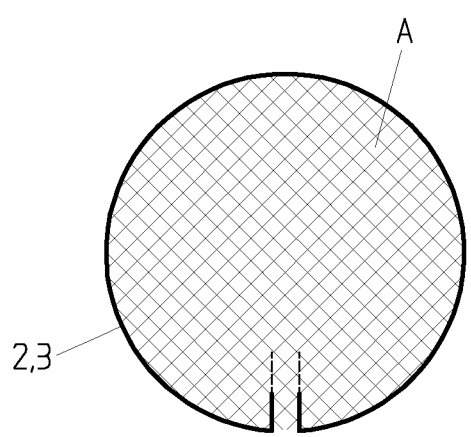
FIGS. 5a and 5b illustrate two possible variant embodiment for the configuration of a passive and/or of an active strain gage according to the invention.
Figure 5B:
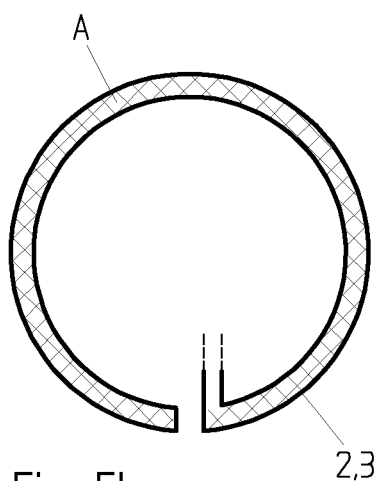

This is illustrated in FIG. 5b by way of an illustrative but in no way limiting example of a correspondingly configured active or passive gage 2,3. In this example, the portion of the gage 2,3 that is configured for at least partly encircling the center of the contact lens is made of two concentric circular segments that are connected to each other on one side and are configured to be each connected to the microprocessor on the other side. In this example, the gage 2,3 thus comprises two concentric loops for at least partly encircling the center of the contact lens, and it is configured to be connected with both ends on the same side to the microprocessor 5. An advantage of this configuration is that, by increasing the number of loops of the portion of the gage 2,3 that is configured for at least partly encircling the center of the contact lens, the overall length of the strain gage 2,3 is increased, thereby increasing its sensitivity to mechanical deformations. Another advantage is that the area A defined by the electrical conductor of the gage 2,3 is significantly reduced in comparison to the area defined by the conductor of the gage illustrated for example in FIG. 5a, thereby reducing the sensitivity of the gage 2,3 of FIG. 5b to electromagnetic perturbations that could induce electrical currents in the gage 2,3 and thus perturb the measurement of the variations of its electrical properties due to mechanical deformations.

Figure 6:
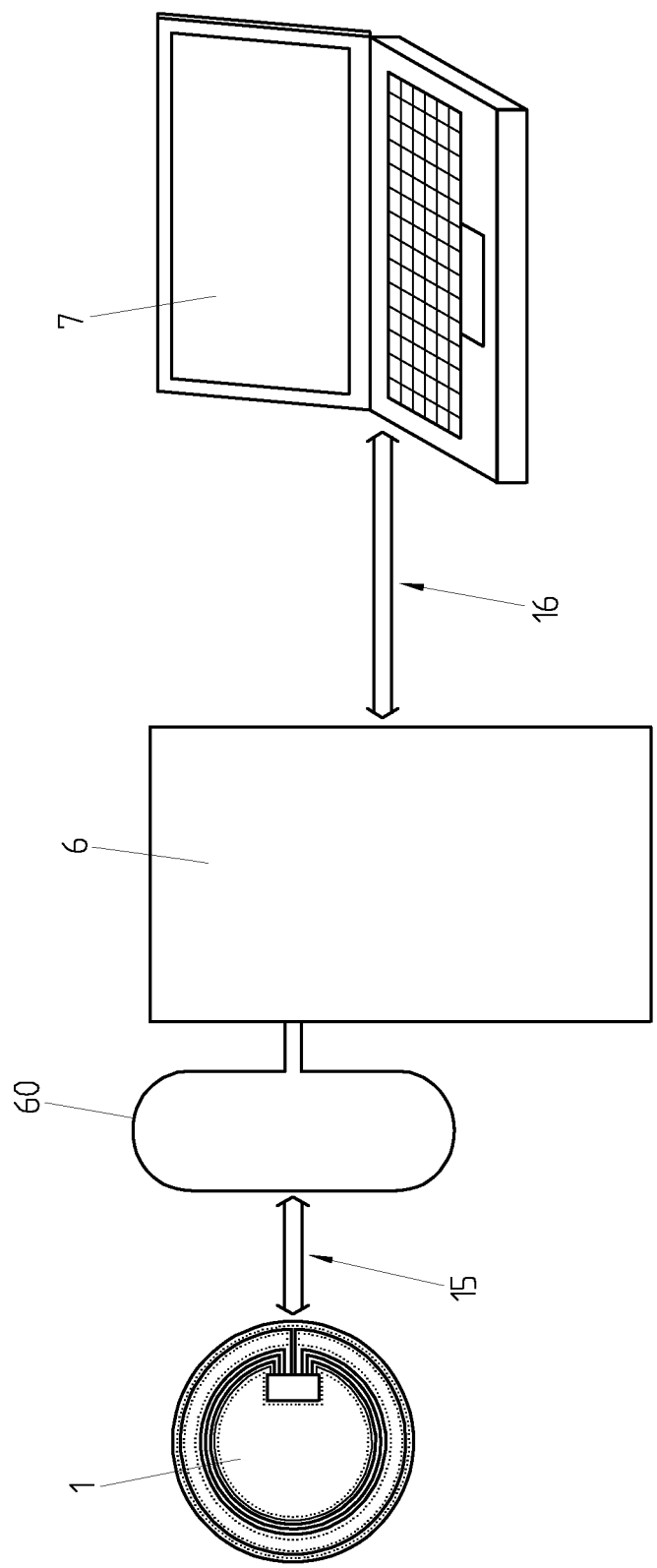
FIG. 6 is a schematic representation of an intraocular pressure monitoring system according to the invention.

FIG. 6 is a schematic representation of a typical intraocular pressure monitoring system using the intraocular pressure monitoring device of the invention. According to the illustrated embodiment, the intraocular pressure monitoring system comprises the intraocular pressure monitoring device of the invention in the form of a contact lens 1 with a pressure sensor, a portable recording device 6 for communicating with the intraocular pressure monitoring device and storing the collected information during the IOP monitoring phases, and a computing device 7, for example a personal computer, for storing, analyzing, computing and/or displaying the data collected and stored by the portable communication device 6.

The portable recording device 6 comprises a first communication interface for communicating with the intraocular pressure monitoring device of the invention. The first communication interface is for example a wireless communication interface comprising an antenna 60 that is advantageously placed near the contact lens 1 when the intraocular pressure monitoring device of the invention is worn by a user. The antenna 60 is for example integrated into eyeglasses, not represented on the figures, and/or into a preferably disposable, flexible and hypoallergenic patch, also not represented on the figures, that are or is worn by the user during the IOP monitoring periods. Other means are however possible within the frame of the invention for placing the antenna 60 at a suitable distance from the intraocular pressure monitoring device of the invention when it is worn by a user. The portable recording device 6 further comprises a second communication interface for communicating with the computing device 7.

When monitoring IOP, the user wears the intraocular pressure monitoring device of the invention by placing the contact lens 1 on his or her eye, just like any ordinary contact lens, and carries the portable recording device 6, for example in a pocket or by hanging it around his or her neck. The antenna 60 is placed as close as possible to the user's eye wearing the contact lens 1 in order to allow the establishment of a first wireless communication channel 15 between the intraocular pressure monitoring device and the recording device 6. Preferably, the antenna 60 is furthermore oriented in a plane as parallel as possible to the plane of the antenna of the intraocular pressure monitoring device of the invention in order to allow for an efficient powering of the pressure sensor over the communication channel 15, which is for example a close distance inductive communication channel 15. The antenna is for example integrated in eyeglasses, and/or into a patch, preferably into a disposable, flexible and hypoallergenic patch, surrounding the eye, and/or in a cap or in another piece of clothing or accessory worn by the user. Preferably, the antenna 60 is centered with the antenna of the intraocular pressure monitoring device of the invention when the intraocular pressure monitoring device and the portable recording device 6 are worn by the user. The diameter of the antenna 60 of the portable recording device 6 is preferably larger than the diameter of the intraocular pressure monitoring device. The shape of the antenna 60 of the portable recording device 6 is for example round, oval, rectangular, or any other appropriate shape. The shape of the antenna 60 of the portable recording device 6 is preferably adapted to the shape of the device, for example the eyeglasses, the patch, the piece of garment, etc., to which it is attached.

According to a preferred embodiment, while monitoring IOP, the portable recording device 6 powers the intraocular pressure monitoring device through the first communication channel 15 at preferably regularly spaced time intervals and collects data sent by the microprocessor through the antenna of the intraocular pressure monitoring device. Collected data for example comprises electrical resistance values of the gages of the pressure sensor and/or a calculated IOP value. The collected data is stored in internal memory of the portable recording device 6. The intraocular pressure is for example measured at a frequency of 10 to 20 Hz during 10 to 60 seconds every 5 to 10 minutes. This allows a precise monitoring of the IOP variations over extended periods of time, including at night, while the user is asleep.

At some preferably predefined moments in time, for example once a day, once a week or once a month, the user and/or a practitioner connects the portable recording device 6 to a computing device 7, for example a personal computer, over a second, preferably wireless, communication channel 16, for example a Bluetooth communication channel. The second communication channel 16 can however also be a wired communication channel, for example a USB or any other appropriate communication channel. The data collected and stored in the internal memory of the portable recording device 6 is then transferred over the second communication channel 16 to the computing device 7 for further analysis and/or computing by the user and/or by the practitioner.

The invention claimed is:

1. Intraocular pressure monitoring device comprising a soft contact lens and a pressure sensor united with said contact lens, said pressure sensor comprising:
    an active strain gage configured to sense deformations of a user's eyeball, and thus of the contact lens, that are due to variations of the user's eyeball intraocular pressure (IOP),
    a passive strain gage,
    a rigid element, and
    a microprocessor,
    said active strain gage, passive strain gage and rigid element being placed at a distance
    from a center of the contact lens, said active strain gage comprising a portion encircling said center of the contact lens by at least 180°,
    wherein:
    a portion of said passive strain gage and a portion of said rigid element each encircle said center of the contact lens by at least 180°,
    said portion of said passive strain gage situated around said center of the contact lens is placed in a region of the contact lens that is rigidified by said portion of said rigid element situated around said center of the contact lens, and
    wherein the passive strain gage is closer to the rigid element than is the active strain gage, to prevent the passive strain gage from deformations due to IOP variations, and
    the rigid element and the passive strain gage are closer to the center than is the active strain gage.

2. Intraocular pressure monitoring device according to claim 1,
    wherein said portion of said active strain gage encircles said center by at least 270°.

3. Intraocular pressure monitoring device according to claim 1,
    wherein said portion of said passive strain gage and said portion of said rigid element each encircles said center by at least 270°.

4. Intraocular pressure monitoring device according to claim 1, wherein said portion of said passive strain gage encircling said center comprises a circular segment.

5. Intraocular pressure monitoring device according to claim 1, wherein said portion of said passive strain gage encircling said center comprises a plurality of rectilinear segments.

6. Intraocular pressure monitoring device according to claim 5, wherein said plurality of rectilinear segments forms a part of a regular polygon.

7. Intraocular pressure monitoring device according to claim 1, wherein said active strain gage, passive strain gage and rigid element are concentric.

8. Intraocular pressure monitoring device according to claim 1,
    wherein said rigid element is an antenna configured to allow wireless communications between said microprocessor and an external device and/or to power said microprocessor.

9. The intraocular pressure monitoring device according to claim 1, wherein:
    the contact lens has a convex outer surface portion and an opposite concave inner surface portion.

10. The intraocular pressure monitoring device according to claim 9, wherein:
    the contact lens comprises a silicone-based material.

11. Intraocular pressure monitoring device according to claim 1, wherein:
    the contact lens comprises a silicone-based material.

12. Intraocular pressure monitoring device according to claim 1, wherein:
    the active strain gage is a first active strain gage and the device includes a second active strain gage;
    the passive strain gage is a first passive strain gage and the device includes a second passive strain gage; and
    the first active strain gage, second active strain gage, first passive strain gage, and second passive strain gage are interconnected in a Wheatstone bridge configuration.

13. Intraocular pressure monitoring device according to claim 1, wherein the active strain gage and the passive strain gage are of similar shape to each other.

14. Intraocular pressure monitoring device according to claim 1, wherein:
    the passive gage consists essentially of one or more circular segments or essentially of a portion of a hexagon, octagon, or dodecagon.

15. Intraocular pressure monitoring device according to claim 1, wherein said passive strain gage is closer than said rigid element to said center of said contact lens.

16. Intraocular pressure monitoring device according to claim 1, further comprising respective connections extending radially inward from the passive strain gage and the active strain gage to the microprocessor.

17. Intraocular pressure monitoring device according to claim 1, wherein the rigid element is an antenna and the device further comprises respective connections extending radially inward from the passive strain gage, the active strain gage, and the rigid element to the microprocessor.

18. Kit comprising:
    a pressure monitoring device according to claim 1; and
    a portable recording device configured for communicating with said pressure monitoring device and for storing data received from said pressure monitoring device.

19. Kit according to the claim 18, wherein said portable recording device is configured for powering said pressure monitoring device over a wireless inductive communication channel.

20. Intraocular pressure monitoring system comprising:
    a pressure monitoring device according to claim 1;
    a portable recording device configured for communicating with said pressure monitoring device and for storing data received from said pressure monitoring device; and
    a computing device configured for communicating with said portable recording device for receiving and/or processing and/or storing data received from said portable recording device.

21. Intraocular pressure monitoring system according to claim 20, wherein said portable recording device is configured for powering said pressure monitoring device over a wireless inductive communication channel.

22. Intraocular pressure monitoring device comprising a soft contact lens and a pressure sensor united with said contact lens, said pressure sensor comprising:
    an active strain gage configured to sense deformations of a user's eyeball, and thus of the contact lens, that are due to variations of the user's eyeball intraocular pressure (IOP),
    a passive strain gage,
    a rigid element, and a microprocessor,
said active strain gage, passive strain gage and rigid element being placed at a distance
from a center of the contact lens, said active strain gage comprising a portion encircling said center of the contact lens by at least 180°,
wherein:
said passive strain gage and said rigid element each comprise a portion encircling said center of the contact lens by at least 270°,
the passive strain gage is closer to the rigid element than is the active strain gage to prevent the passive strain gage from deformations due to IOP variations,
the rigid element and the passive strain gage are closer to the center than is the active strain gage.

* * * * *